United States Patent

Bull et al.

[11] Patent Number: 5,587,496
[45] Date of Patent: Dec. 24, 1996

[54] 15,15-DIALKYL-SUBSTITUTED DERIVATIVES OF ESTRADIOL

[75] Inventors: James R. Bull, Cape Town, South Africa; Karl-Heinrich Fritzmeier; Christa Hegele-Hartung, both of Berlin, Germany

[73] Assignee: Schering Aktiengesellschaft, Berlin, Germany

[21] Appl. No.: 284,786

[22] Filed: Aug. 2, 1994

[30] Foreign Application Priority Data

Aug. 2, 1993 [DE] Germany .................. 43 26 240.6

[51] Int. Cl.⁶ .................................................. C07J 1/00
[52] U.S. Cl. ................................................ 552/629
[58] Field of Search ...................................... 552/629

[56] References Cited

U.S. PATENT DOCUMENTS 3,766,224  10/1973  Coombs ........................ 260/397.4
4,231,946  11/1980  Ponsold et al. .................. 260/397.4

OTHER PUBLICATIONS

Groen et al., Recueil de Travaux Chimiques des Pays–Bas, vol. 98, No. 4, pp. 239–242 (Apr. 1979).
Tetrahedron, vol. 47, No. 37, pp. 7751–7766 (Sep. 9, 1991).

*Primary Examiner*—Philip Tucker
*Assistant Examiner*—Catherine Kilby Scalzo
*Attorney, Agent, or Firm*—Millen, White, Zelane, & Branigan, P.C.

[57] ABSTRACT

New 15,15-dialkyl-substituted derivatives of the estradiol of general formula I

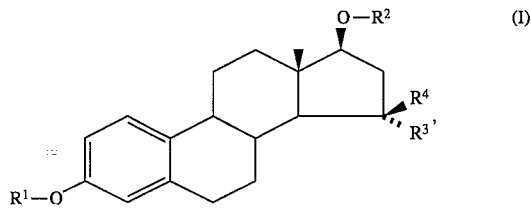

in which $R^1$ and $R^2$, independently of one another, are each a hydrogen atom or a straight-chain alkanoyl group with 1 to 10 carbon atoms, a branched-chain alkanoyl group with 3–10 carbon atoms, an alkanoyl group of 3–10 carbon atoms containing a cycloaliphatic structure of 3–6 carbon ring atoms or a benzoyl group, and $R^3$ and $R^4$, independently of one another, are each a straight-chain alkyl group with 1 to 10 carbon atoms or a branched-chain alkyl group with 3 to 10 carbon atoms, are described, a process for their production and initial products for this process.

The new compounds have—also after oral administration—high estrogenic effectiveness and are suitable for the production of pharmaceutical agents.

13 Claims, 1 Drawing Sheet

15,15-DIALKYL-SUBSTITUTED DERIVATIVES OF ESTRADIOL

This invention relates to the new 15,15-dialkyl-substituted derivatives of estradiol of general formula I

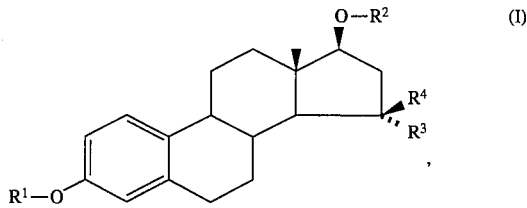

in which

R$^1$ and R$^2$, independently of one another, are each a hydrogen atom, a straight-chain alkanoyl group with 1 to 10 carbon atoms, a branched-chain alkanoyl group with 3 to 10 carbon atoms, an alkanoyl group of 3–10 carbon atoms containing a cycloaliphatic structure of 3–6 carbon ring atoms, or a benzoyl group, and R$^3$ and R$^4$, independently of one another, are each a straight-chain alkyl group with 1 to 10 carbon atoms or a branched-chain alkyl group with 3 to 10 carbon atoms.

Radicals R$^1$ and R$^2$ can be identical or different.

Radicals R$^1$ and/or R$^1$ preferably stand for a hydrogen atom.

As acyl groups R$^1$ and R$^2$, radicals from organic carboxylic acids with 1 to 10 carbon atoms are suitable. Such radicals are derived from aliphatic, cycloaliphatic, aliphatic-cycloaliphatic and aromatic monocarboxylic acids. The number of carbon atoms in the ring structures can vary from 3 to 6. As radicals R$^1$ and R$^2$, the acyl groups of acetic acid, propionic acid, butyric acid, isobutyric acid, pivalic acid, caproic acid, heptanoic acid, caprylic acid, pelargonic acid, decanoic acid, 3-cyclopentylpropionic acid and benzoic acid are preferred.

For radicals R$^3$ and R$^4$, methyl, ethyl, propyl, isopropyl, butyl, isobutyl and tert-butyl groups are preferred. But, the higher, homologous straight-chain and branched-chain alkyl groups up to a decyl radical are also suitable.

The R$^3$ and R$^4$ radicals can be identical or different.

In particular, carbon atom 15 is preferably substituted by two methyl groups. As an especially preferred compound according to the invention, 15,15-dimethyl-estra-1,3,5(10)-triene-3,17β-diol can be mentioned.

The compounds of general formula I according to the invention exhibit a strong affinity to the estrogen receptor and, in particular, also have high estrogenic effectiveness after oral administration.

As compounds with high estrogenic effectiveness, for example, the natural estrogens estradiol and estriol (E. Schröder, C. Rufer and R. Schmiechen, Pharmazeutische Chemie [Pharmaceutical Chemistry], 1982, Georg Thieme Verlag, Stuttgart-New York, p. 568 ff) are known. But, they are metabolically not stable and after oral administration, are catabolized by oxidation of the 17-hydroxy group to the corresponding, less effective estrone derivative. Based on this quick metabolic inactivation, they are hardly suitable for oral use.

By introducing, for example, an ethinyl group on the 17-C atom (ethinylestradiol, loc. cit., p. 574), the oxidation of the 17-hydroxy group can be prevented, and the corresponding derivatives consequently have at their disposal high estrogenic effectiveness after peroral administration.

Only recently has it been possible to obtain estrogenic compounds with high peroral effectiveness, not by variations of the substituents on the steroid skeleton, but by modification of the steroid skeleton itself. The bridging of the 14- and 17-carbon atoms of the estradiol with an etheno- or ethano bridge thus blocks the oxidation of the 17β-hydroxy group (J. Chem. Commun., 1986, 451–453 or International Patent Application PCT/DE 87/00361).

Derivatives of the estradiol, which carry a 14 α, 15α-methylene group, also represent compounds with high estrogenic effectiveness after oral administration (U.S. Pat No. 4,231,946).

After oral administration, the estrogenic action of the compounds of general formula I according to the invention is comparable with that of the standard 17α-ethinylestradiol. In the compounds according to the invention, the attack of the steroid-17β-dehydrogenase is blocked by the introduction of two alkyl groups in C-15-position and thus impedes the metabolic oxidation of the 17-hydroxy group despite the presence of a hydrogen atom on the 17-C atom.

BRIEF DESCRIPTION OF THE DRAWING

Various other objects, features and attendant advantages of the present invention will be more fully appreciated as the same becomes better understood when considered in conjunction with the accompanying drawing wherein.

DETAILED DESCRIPTION

Figure 1:
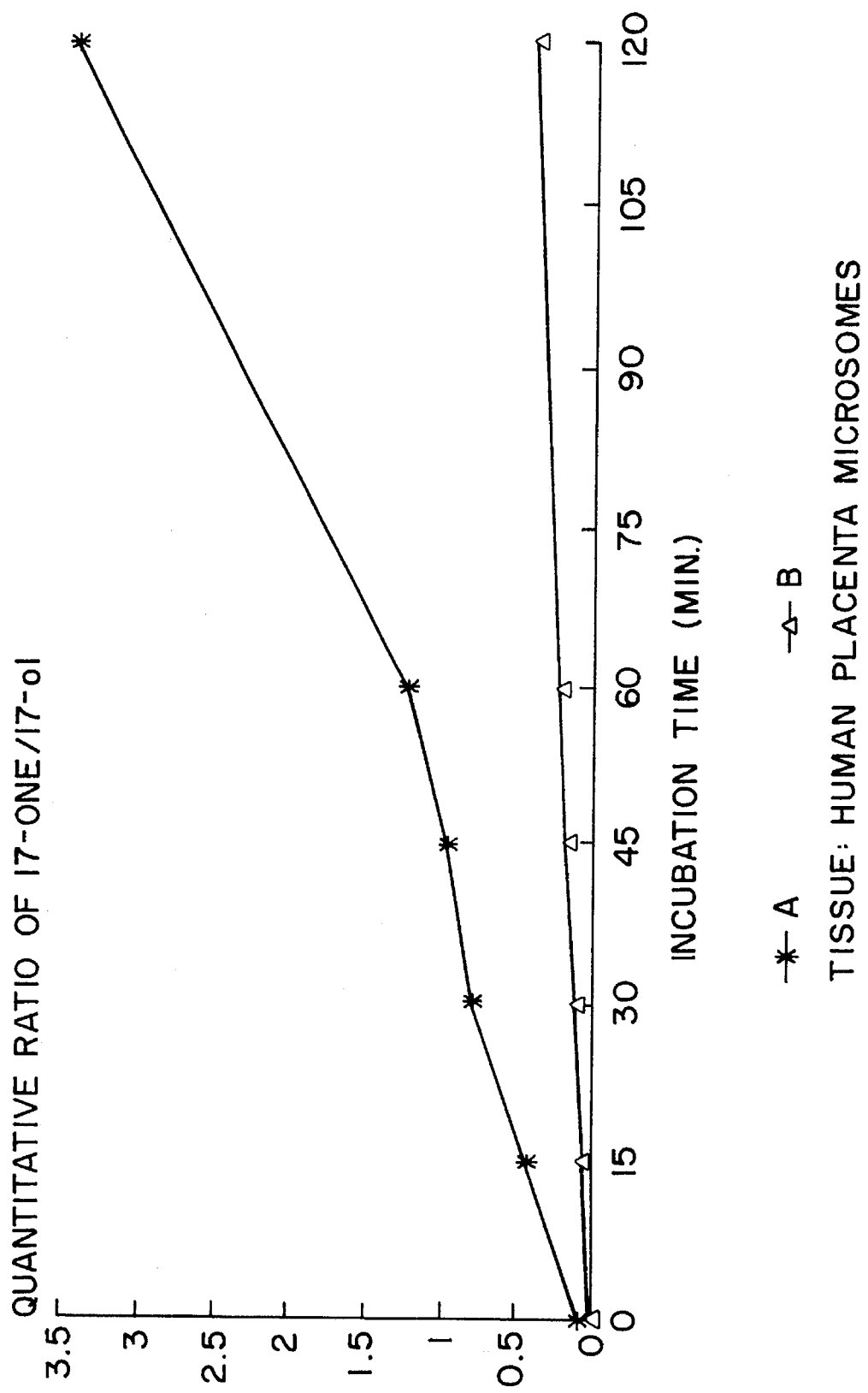
FIG. 1 is a graph demonstrating the stability of estradiol and 15,15-dimethyl-estra-1,3,5(10)-triene-3,17β-diol with respect to 17β-hydroxysteroid dehydrogenase.

To determine the stability of estradiol (A) itself as well as of a compound according to the invention, i.e., 15,15-dimethyl-estra-1,3,5(10)-triene-3,17β-diol (B), against 17β-hydroxysteroid dehydrogenase from human placenta, the test substances are incubated with placenta microsomes in the presence of NADP (nicotinamide-adeninedinucleotide phosphate; 0.5 mmol).

The steroids (initial substrate and product) are extracted and separated by HPLC. For evaluation, the quotients are formed from the electronically integrated peak areas of the corresponding reaction product (namely the assumed 17-keto compound) and the initial substance and plotted against the incubation time (FIG. 1). While estradiol (A) is converted to the estrone by the 17β-hydroxysteroid dehydrogenase to a considerable extent, the compound according to the invention 15,15-dimethyl-estra-1,3,5(10)-triene-3,17β-diol (B) represents an only moderate substrate for the 17β-hydroxysteroid dehydrogenase.

This can explain the oral effectiveness of the newly described substances.

The estrogenic effectiveness of the compounds according to the invention can be shown by the results of the estrogen receptor binding test. In this known in vitro test, tissue from rat uteri is prepared and radioactively-labeled $^3$H-estradiol is used as reference substance. The compound according to the invention 15,15-dimethyl-estra-1,3,5(10)-triene-3,17β-diol accordingly has a competition factor K of 1.5.

The invention also relates to the use of the compounds of general formula I for the production of pharmaceutical agents.

The compounds according to the invention can be formulated and used in the same way as ethinylestradiol, which is the most used estrogen. They are processed to the usual forms of pharmaceutical agents with the additives, vehicles and/or flavoring substances usual in galenical pharmacy according to methods known in the art. For oral administration, especially tablets, coated tablets, capsules, pills, suspensions or solutions are suitable. For parenteral administration, especially oily solutions, such as, for example, sesame oil or castor oil solutions, are suitable, which can optionally contain in addition a diluent, such as, for example, benzyl benzoate or benzyl alcohol.

The active ingredient concentration in the pharmaceutical compositions is a function of the form of administration and the field of application. Thus, for example, capsules or tablets for treating estrogen deficiency symptoms can contain about 0.001–0.05 mg of active ingredient, oily solutions for intramuscular injection can contain about 0.01–0.1 mg of active ingredient per 1 ml and vaginal ointments can contain about 0.1–10 mg per 100 ml of ointment. For contraception in the female, the estrogens according to the invention can be used in combination with the gestagens typically used in hormonal contraceptives or proposed for use in such preparations, e.g., progesterone, medroxyprogesterone acetate, gestonorone caproate, chlormadinone acetate, lynestrenol, hydroxyprogesterone caproate, norethindrone and its esters (e.g., acetate), norgestrel, laevonorgestrel, cyproterone acetate, desogestrel, norgestimate, dihydrospirorenone and gestodene. Tablets or coated tablets for daily intake of a tablet or a coated tablet preferably contain about 0.003–0.05 mg of the estrogen according to the invention and preferably about 0.05–0.5 mg of a gestagen.

The compounds according to the invention can be used in the case of estrogen deficiency symptoms of the female, such as, for example, amenorrhea, dysmenorrhea, sterility, endometritis, colpitis and climacteric symptoms (hormone replacement therapy) and for the prevention of osteoporosis. Further, the compounds can be used as estrogenic components in hormonal contraceptives (single-phase and multi-phase and multi-stage preparations). Furthermore, they are suitable in connection with other active ingredients for use in hormone-carrying intrauterine pessaries, implantable active ingredient vehicles as well as in transdermal administration systems. Possible fields of use of the compounds of general formula I according to the invention in such transdermal systems are female birth control and hormone replacement therapy (HRT).

The increased fat solubility, in comparison to estradiol and 17α-ethinylestradiol, based on the lipophilic alkyl groups in 15-position, makes the compounds according to the invention especially suitable for use in such depot formulations.

The new compounds of general formula I

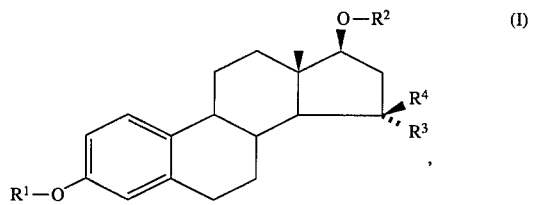

in which $R^1$ and $R^2$, independently of one another, are each a hydrogen atom, a straight-chain alkanoyl group with 1 to 10 carbon atoms, a branched-chain alkanoyl group with 3 to 10 carbon atoms, an alkanoyl group of 3–10 carbon atoms containing a cycloaliphatic structure of 3–6 carbon ring atoms, or a benzoyl group, and $R^3$ and $R^4$, independently of one another, are each a straight-chain alkyl group with 1 to 10 carbon atoms or a branched-chain alkyl group with 3 to 10 carbon atoms, are produced, by a process wherein the 3-alkylether of a compound of general formula II

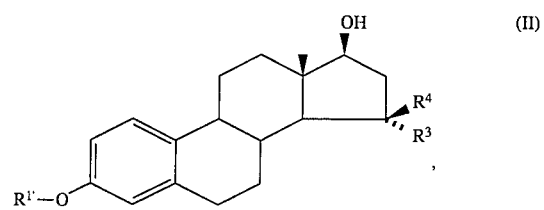

in which $R^{1'}$ is a straight-chain alkyl group with 1 to 10 carbon atoms or a branched-chain alkyl group of 3 to 10 carbon atoms, and $R^3$ and $R^4$ have the meaning indicated in formula I, is cleaved according to standard processes. Optionally the 3-hydroxy group is esterified and then, subsequently, the 17-hydroxy group is optionally esterified. Alternatively, the 3- and 17-hydroxy groups are optionally simultaneously esterified and optionally the resultant 3,17-diacyloxy is selectively saponified to a 3-hydroxy-17-acyloxy compound.

Alkyl groups for $R^{1'}$ with up to 10 carbon atoms are, for example, methyl, ethyl, propyl, isopropyl, butyl, isobutyl or tert-butyl or else a higher homologue of the above-mentioned groups. A methyl group is preferred.

The cleavage of the 3-alkylether is performed according to conventional methods of steroid ether cleavage. Thus, the 3-alkyl ether cleavage can be performed in the boiling heat, for example, with a Lewis acid in an inert solvent. As Lewis acids, for example, boron trifluoride etherate or diisobutylaluminum hydride (DIBAH) are suitable. As solvents, benzene, toluene, tetrahydrofuran, dioxane, i.a., are suitable.

For the subsequent optional esterification of the phenolic and tertiary hydroxy group, the known processes used for esterification in steroid chemistry can be employed.

The esterification is performed, for example, by reaction with a corresponding carboxylic acid halide (chloride or bromide) or carboxylic acid anhydride (carbon number depending on the ultimately desired $R^1$ and/or $R^2$) in the presence of a base such as, for example, 4-dimethylaminopyridine at a temperature of preferably about 20°–80° C. If pyridine and 4-dimethylaminopyridine are used together as tertiary amines, the esterification can be performed with low carboxylic acid radicals, preferably at about room temperature and with higher carboxylic acids, preferably at about 40°–80° C. As an example, the reaction with acetic acid or acetic anhydride in the presence of strong acids, such as, for example, trifluoroacetic acid, perchloric acid or p-toluenesulfonic acid, at room temperature or somewhat elevated temperature can also be mentioned.

The syntheses of the two possible semi-esters take place by partial esterification or partial saponification:

a) Starting from 3,17β-dihydroxy compounds, the 3-acyloxy-17β-hydroxy compounds can be obtained by selective esterification of the phenolic hydroxy group. The reactions are achieved by reacting the corresponding acid anhydride in the presence of a heterocyclic nitrogen aromatic compound, preferably pyridine. Suitable reaction temperatures are, for example, about room temperature to boiling temperature of the reaction mixture. Selective esterification of the 3-hydroxy group can also be controlled by the amount of esterification reagent supplied.

b) Starting from 3,17β-diacyloxy compounds, the 3-hydroxy-17α-acyloxy compounds can be obtained by selective saponification of the phenolic acyloxy group.

Synthesis takes place by reaction with an alkali carbonate or alkaline-earth carbonate, preferably potassium carbonate or calcium carbonate, in aqueous-methanolic solution. The reaction temperature can be, for example, room temperature to boiling temperature of the reaction mixture.

Production of the compounds according to the invention is represented in the diagram below, from which the variation of the stereochemistry on carbon atom 15 can also be seen.

For this purpose, the process described for the production of 3-methoxy-15β-methyl-estra-1,3,5(10)-trien-17one (R. V. Coombs, U.S. Pat. No. 3,766,224; Chem. Abstr. 1974, 80, 27436k) is modified. See the following reaction scheme.

The enolate obtained by adding lithium dialkyl cuprate LiCuR$_2^3$ or the corresponding alkylmagnesium halide (alkyl=R$^3$, halide=Br, I) under copper(I) catalysis (for example, CuI, CuCN) to 3-methoxy-estra-1,3,5(10),15-tetraene-17-one (compound 1), is converted in situ by adding trimethylchlorosilane to the corresponding silylenol ether, which is reacted—optionally without further purification—with palladium acetate in the sense of a Tsuji dehydrogenation (J. Tsuji et al., Chem. Letters 1133, 1984) to 3-methoxy-15-alkyl-estra-1,3,5(10),15-tetraene (see compound 3, 7 or 10). By another addition now of the lithium dialkyl cuprate LiCuR$_2^4$ or of the corresponding alkylmagnesium halide (alkyl=R$^4$, halide=Br, I) under copper(I) catalysis (for example, CuI, CuCN) to unsaturated ketone (see compound 3, 7 or 10), the 15,15-dialkyl-substituted compound (see compound 4, 5, 8 or 11) is obtained, which is converted by reduction of the C-17-carbonyl group according to standard processes to 17β-hydroxy compound (see compound 12, 13, 14 or 15), an initial compound of general formula II.

By using the corresponding dialkyl lithium cuprates, radicals R$^3$ and R$^4$ can be varied as desired within the scope of general formula I and by the analogous course of action for the production of compound 12, 13, 14 or 15, the initial compounds of general formula II required for synthesis of all compounds of general formula I are available.

While the above discussion describes preparation of 3-methoxy compounds of formula II, the other 3-alkoxy compounds of formula II can be prepared by using the appropriate higher 3-alkoxy homologues of compound 1 as the starting material. See U.S. Pat. No. 3,766,224.

If R$^3$ and R$^4$ are to be different, the stereochemistry on carbon atom 15 can be controlled by the sequence of the alkylation steps. Group R$^3$, the first of the two groups added to the C15 position, is located in the final end product in α-position.

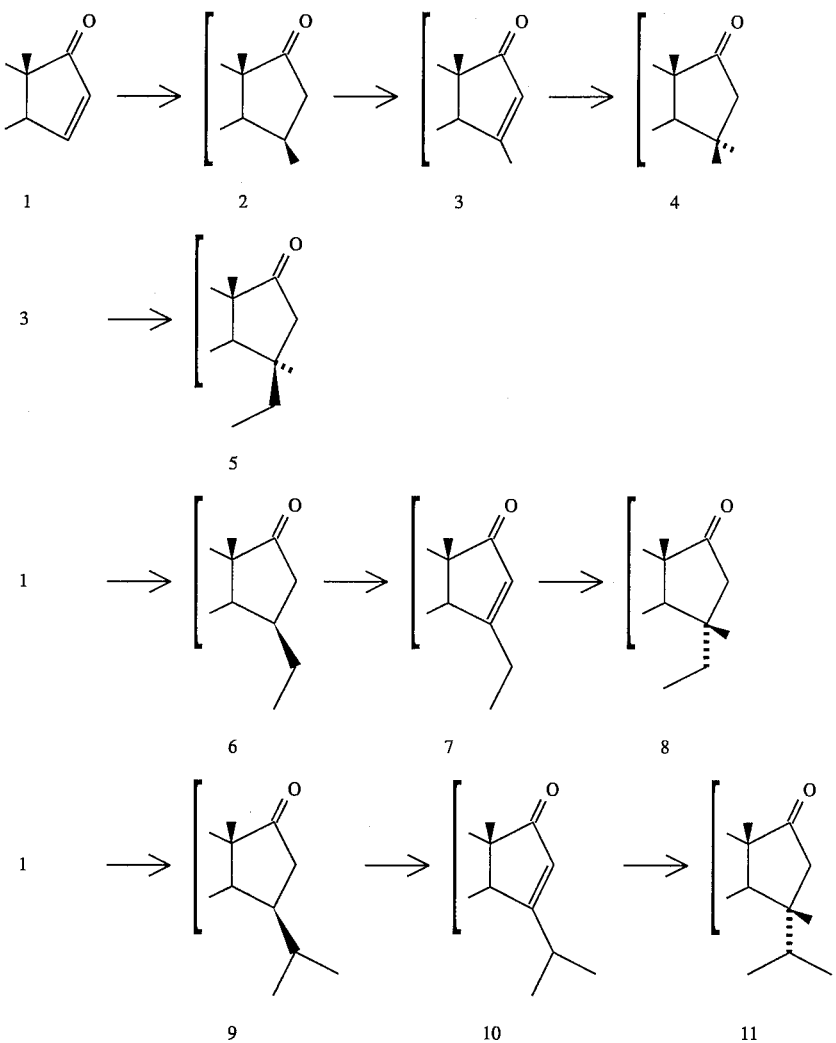

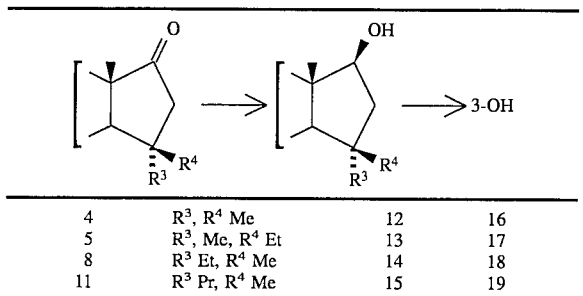

| | | | |
|---|---|---|---|
| 4 | $R^3$, $R^4$ Me | 12 | 16 |
| 5 | $R^3$, Me, $R^4$ Et | 13 | 17 |
| 8 | $R^3$ Et, $R^4$ Me | 14 | 18 |
| 11 | $R^3$ Pr, $R^4$ Me | 15 | 19 |

The 17β-hydroxy compounds of general formula II and the 17-keto compounds passed through for their synthesis are novel and—taken together as initial compounds of general formula IIa—also belong to the object of this invention.

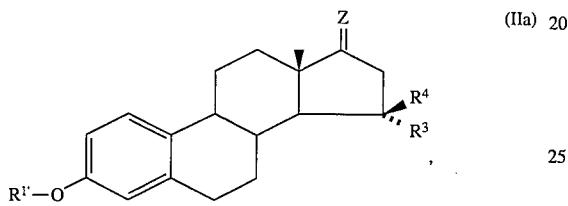

wherein $R^{1'}$ is a straight-chain alkyl having 1–10 carbon atoms or a branched-chain alkyl group having 3–10 carbon atoms;

$R^3$ and $R^4$, independently of one another, are each a straight-chain alkyl having 1–10 carbon atoms or a branched-chain alkyl having 3–10 carbon atoms; and is an α-hydrogen atom and a β-hydroxy group or a keto-oxygen atom.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above, and of corresponding German application P 43 26 240.6, filed Aug. 2, 1993, are hereby incorporated by reference.

EXAMPLES

The following examples are used for a more detailed explanation of the invention:

Example 1

3-Methoxy-15β-methylestra-1,3,5(10)-trien-17-one (2)

Lithium dimethylcuprate (0.63 mmol) in dry diethyl ether (1 ml) [prepared from copper(I) iodide (120 mg; 0.63 mmol) and methyl lithium (0.75 ml; 1.6M; 1.20 mmol)] was cooled to −78° C. Triethylamine (0.1 ml; 0.8 mmol) and chlorotrimethylsilane (0.1 ml; 0.78 mmol) were added, followed by the $\Delta^{15}$-17-ketone (1) (84 mg; 0.30 mmol) in dry tetrahydrofuran (4 ml). After 5 min., saturated aqueous ammonium chloride and 1M hydrochloric acid were added. The reaction mixture was stirred at 20° C. for 15 min. The residue upon work-up (ethyl acetate) (72 mg) was chromatographed on silica gel (6 g), and eluting with ethyl acetate-toluene (1:4) gives 3-methoxy-15β-methylestra-1,3,5 (10)-trien-17-one (2) (65 mg; 92%), m.p. 127°–129° C. (from acetone-methanol) (lit.,[1] m.p. 122°–124° C.); $[\alpha]_D$+74° (C 1.0); $\nu_{max}$ 1725 cm$^{-1}$ (CO); $\delta_H$ 1.07 (3H, s, 13β-Me); 1.16 (3H, d, J 7.4 Hz, 15β-Me), 2.91 (2H, m, 6-H$_2$), 3.79 (3H, s, 3-OMe), 6.69 (1H, d, J 2.7 Hz, 4-H), 6.73 (1H, dd, J 8.6 and 2.7 Hz, 2-H), and 7.21 (1H, d, J 8.6 Hz, 1-H); $\delta_c$ 17.0 (15-Me), 17.9 (C-18), 25.6 (C-15), 26.8 (C-11), 27.7 (C-7), 29.5 (C-8), 34.1 (C-16), 35.9 (C-12), 44.5 (C-6), 44.8 (C-9), 47.5 (C-13), 55.2 (3-OMe), 111.4 (C-2), 113.9 (C-4), 126.0 (C-1), 132.5 (C-10), 137.8 (C-5), 157.7 (C-3), and 221.3 (C-17) (Found: C, 80.7; H, 8.6%; M$^+$, 298. $C_{20}H_{26}O_2$ requires C, 80.5; H, 8.8%; M, 298).

3-Methoxy-15-methylestra-1,3,5(10),15,tetraen-17-one (3)

(a) A solution of lithium diisopropylamide (5.28 mmol) in dry tetrahydrofuran (4 ml) [prepared at 0° C. from diisopropylamine (1.5 ml; 10.58 mmol) in dry tetrahydrofuron (4 ml) and butyl lithium (3.3 ml; 1.6M; 5.28 mmol)] was cooled to −78° C. and the 15β-methyl-17-ketone (2) (315 mg; 1.05 mmol) in dry tetrahydrofuran (5 ml) was slowly added. Stirring at −78°C. was maintained for 30 min. Chlorotrimethylsilane (1.4 ml; 11.0 mmol) was added and the mixture was allowed to warm to 20° C. After 15 min., the flask was re-cooled to 0° C. and saturated aqueous ammonium chloride was added. The residue upon work-up (ethyl acetate) (385 mg) was dissolved in acetonitrile (10 ml). Palladium(II) acetate (233 mg; 1.04 mmol) was added and the mixture was stirred at refluxing temperature for 15 min. The reaction mixture was cooled to 20° C., filtered and concentrated to give a dark crystalline product (484 mg). Chromatography on silica gel (24 g), with ethyl acetatetoluene (1:19) as eluent gave 3-methoxy-15-methylestra-1,3,5(10),15-tetraen-17-one (3) (267 mg; 86% from 2), m.p. 156°–158° C. (from ethyl acetate-methanol); $[\alpha]_D$ −17° (c 1.0); $\nu_{max}$ 1688 cm$^{-1}$ (CO); $\delta_H$ 1.11 (3H, s, 13β-Me), 2.25 (3H, s, 15-Me), 2.94 (2H, m, 6-H$_2$), 3.79 (3H, s, 3-OMe), 5.77 br (1H, s, 16-H), 6.66 (1H, d, J 2.5 Hz, 4-H), 6.75 (1H, dd, J 8.6 and 2.5 Hz, 2-H), and 7.23 (1H, d, J 8.6 Hz, 1-H); $\delta_c$ 20.9 (C-18), 21.5 (15-Me), 25.6 (C-11), 27.7 (C-7), 29.2 (C-9), 29.3 (C-8), 36.8 (C-12), 45.2 (C-6), 52.6 (C-13), 55.2 (3-OMe), 57.3 (C-14), 111.5 (C-2), 113.6 (C-4), 126.1 (C-1), 128.7 (C-16), 132.0 (C-10), 137.3 (C-5), 157.7 (C-3), 175.2 (C-15), and 212.1 (C-17) (Found: C, 81.3, H, 8.15%; M$^+$, 296. $C_{20}H_{24}O_2$ requires C, 81.0; H, 8.2%; M, 296).

(b) Lithium dimethylcuprate (0.79 mmol) in dry diethyl ether (1 ml) was prepared as described previously. The reagent was cooled to −78° C., triethylamine (0.1 ml; 0.8 mmol) and chlorotrimethylsilane (0.1 ml; 0.78 mmol) were added, followed by the $\Delta^{15}$-17-ketone (1) (106 mg; 0.37 mmol) in dry tetrahydrofuran (4 ml). After 5 min., saturated aqueous ammonium chloride was added. The residue upon work-up (ethyl acetate) comprised a colorless oil (109 mg). This product was treated under similar conditions of dehydrosilylation as detailed above [66 mg palladium(II) acetate in 5 ml acetonitrile], to yield the 15-methyl-$\Delta^{15}$-17-ketone (3) (93 mg; 85% from 1).

3-Methoxy-15,15-dimethylestra-1,3,5(10)-trien-17-one (4)

To a solution of lithium dimethylcuprate (0.79 mmol) in dry diethyl ether (2 ml) [conventionally prepared at 0° C. from copper(I) iodide (150 mg; 0.79 mmol) and methyl lithium (1.3 ml; 1.6M; 2.08 mmol)] at −78° C., boron trifluor-ide-diethyl ether complex (0.1 ml; 0.80 mmol) was added, followed by the 15-methyl-Δ$^{15}$-17-ketone (3) (163 mg; 0.55 mmol) in dry tetrahydrofuran (2 ml). After 30 min., saturated aqueous ammonium chloride was added. The standard work-up (ethyl acetate) gave a crystalline residue, chromatography of which on silica gel (5 g), eluting with ethyl acetate-toluene (1:19) gave the 15,15-dimethylketone (4) (146 mg; 70%), m.p. 145°–148° C. (from ethyl acetate-methanol); [α]$_D$+75° (C 1.0); ν$_{max}$ 1727 cm$^{-1}$ (CO); δ$_H$ 1.10 (3H, s, —β-Me), 1.28 and 1.29 (each 3H, s, 15α- and 15β-Me), 1.84 (1H, d, J 10.9 Hz, 14α-H), 2.09 and 2.61 (each 1H, d, J 19.4 Hz, 16α- and 16β-H), 2.93 (2H, m, 6-H$_2$), 3.78 (3H, s, 3-OMe), 6.63 (1H, d, J 2.7 Hz, 4-H), 6.70 (1H, dd, J 8.6 and 2.7 Hz, 2-H), and 7.21 (1H, d, J 8.6 Hz, 1-H); δ$_c$ 17.8 (C-18), 24.5 (15-Me), 26.0 (C-11), 28.2 (C-7), 29.8 (C-6), 34.2 (C-12), 34.6 (15-Me), 35.5 (C-15), 37.5 (C-8), 44.9 (C-9), 50.2 (C-13), 53.6 (C-16), 55.2 (3-OMe), 58.4 (C-14), 111.6 (C-2), 113.6 (C-4), 126.4 (C-1), 132.2 (C-10), 137.4 (C-5), 157.6 (C-3), and 221.4 (C-17) (Found: C, 80.5; H, 8.8%; M$^+$, 312. C$_{21}$H$_{28}$O$_2$ requires C, 80.7; H, 9.0%; M, 312).

15β-Ethyl-3-methoxy-15α-methylestra-1,3,5 (10)-trien-17-one (5)

A solution of ethylmagnesium iodide (2.5 mmol) in dry diethyl ether (2 ml) [prepared at 20° C. from magnesium (60 mg; 2.5 mmol) and ethyl iodide (0.2 ml; 2.5 mmol)] was cooled to 0° C., copper (I) iodide (47 mg; 0.25 mmol) was added, and the mixture was stirred for 5 min. A solution of the 15-methyl-Δ$^{15}$-17-ketone (3) (148 mg; 0.5 mmol) in dry tetrahydrofuran (2 ml) was added. The reaction mixture was stirred at 20° C. for 15 min. Saturated aqueous ammonium chloride and aqueous ammonia were added, and the residue upon work-up (ethyl acetate) (150 mg; 92%) was crystallized from diisopropyl ether to give 15β-ethyl—3-methoxy-15α-methylestra-1,3,5 (10)-trien-17-one (5) (135 mg), m.p. 104°–107° C. (from diisopropyl ether-methanol) [α]$_D$+90° (c 1.0); ν$_{max}$ 1724 cm$^{-1}$; δ$_H$ 0.94 (3H, t, J 7.6 Hz, 15β-CH$_2$CH$_3$), 1.09 (3H, s, 13β-Me), 1.22 (3H, s, 15β-Me), 1.63 and 1.76 (each 1H, degen. dq., J 15.2 and 3 ×7.6, 15β-CH$_2$CH$_3$), 1.87 and 2.80 (each 1H, d, J 19.3 Hz, 16α- and 16β-H), 2.91 (2H, m, 6-H$_2$), 3.78 (3H, s, 3-OMe), 6.64 (1H, d, J 2.8 Hz, 4-H), 6.71 (1H, dd, J 8.7 and 2.8 Hz, 2-H), and 7.21 (1H, d, J 8.7 Hz, 1-H); δ$_c$ 9.0 (C-15$^2$), 18.3 (C-18), 25.9 (C-15$^1$), 27.4 (C-11), 28.6 (C-7), 29.8 (C-6), 30.3 (C-12), 34.4 (15α-Me), 37.3 (C-8), 39.4 (C-15), 45.1 (C-9), 48.9 (C-16), 49.8 (C-13), 55.2 (3-OMe), 59.8 (C-14), 111.6 (C-2), 113.6 (C-4), 126.4 (C-1), 132.3 (C-10), 137.4 (C-5), 157.6 (C-3), and 220.3 (C-17) (Found: C, 80.9; H, 9.6%; M$^+$, 326. C$_{22}$H$_{30}$O$_2$ requires C, 80.9; H, 9.3%; M, 326).

15β-Tethyl-3-methoxyestra-1,3,5-trien-17-one (6)

A solution of ethylmagnesium iodide (3.8 mmol) in dry diethyl ether (1 ml) [prepared from magnesium (91 mg; 3.8 mmol) and ethyl iodide (0.3 ml; 3.8 mmol)] was cooled to 0° C. Copper(I) iodide (71 mg; 0.37 mmol) was added. A solution of the enone (1) (200 mg; 0.68 mmol) in dry tetrahydrofuran (5 ml) was slowly added, and stirring was maintained at 20° C. for 10 min. The mixture was cooled to 0° C., and saturated aqueous ammonium chloride was added. The residue upon work-up (ethyl acetate) (207 mg; 93%) was recrystallized to give 15β-ethyl-3-methoxyestra-1,3,5 (10)-trien-17-one (6) (198 mg), m.p. 125–129° C. (from chloroform- methanol); [α]$_D$+85° (c 0.95); ν$_{max}$ 1727 cm$^{-1}$ (CO); δ$_H$ 0.95 (3H, t, J 7.5 Hz, 15β-CH$_2$CH$_3$), 1.02 (3H, s, 13β-Me), 1.34 and 1.65 (each 2H, m, 15β-CH$_2$CH$_3$), 1.90 (1H, dd, J 9.3 and 2.7 Hz, 14α-H), 2.39 (2H, m, 16α- and 16β-H), 2.92 (2H, m, 6-H$_2$), 3.79 (3H, s, 3-OMe), 6.66 (1H, d, J 2.9 Hz, 4-H), 6.72 (1H, dd, J 8.4 and 2.9 Hz, 2-H), and 7.20 (1H, d, J 8.4 Hz, 1-H); δ$_c$ 13.9 (C-15$^2$), 17.8 (C-18), 23.8 (C-15$^1$), 25.6 (C-11), 26.8 (C-7), 29.5 (C-6), 34.0 (C-12), 36.0 (C-8), 36.5 (C-15), 42.2 (C-9), 44.6 (C-16), 47.1 (C-13), 52.9 (C-14), 55.2 (3-OMe), 111.4 (C-2), 113.9 (C-4), 126.0 (C-1), 132.4 (C-10), 137.8 (C-5), 157.7 (C-3), and 221.4 (C-17) (Found: C, 80.6; H, 8.9%; M$^+$, 312. C$_{21}$H$_{28}$O$_2$ requires C, 80.7; H, 9.0%; M, 312).

15-Ethyl-3-methoxyestra-1,3,5(10),15-tetraen-17-one (7)

A solution of lithium diisopropylamide (7.8 mmol) in dry tetrahydrofuran (3 ml) [prepared at 0° C. from diisopropylamine (2.2 ml; 15.8 mmol) in tetrahydrofuran (3 ml) and butyl lithium (4.9 ml; 1.6M; 7.8 mmol)] was cooled to −78° C. A solution of the 15β-ethyl ketone (6) (495 mg; 1.58 mmol) in dry tetrahydrofuran (12 ml) was slowly added. After 30 min. at −78° C., chlorotrimethylsilane (2.5 ml; 19.7 mmol) was added and stirring was maintained at 0° C. for 15 min. Saturated aqueous ammonium chloride was added. The residue upon work-up (ethyl acetate) (577 mg) was dissolved in dry acetonitrile (20 ml). Palladium(II) acetate (340 mg; 1.51 mmol) was added and the solution was heated to refluxing temperature for 20 min. The solution was cooled to 20° C., filtered, and evaporated. Chromatography of the residue (470 mg) on silica gel (25 g) and eluting with ethyl acetate (1:19) gave 15-ethyl-3-methoxyestra-1,3,5 (10), 15-tetraen-17-one (7) (419 mg; 85% from 6), m.p. 103–106° C. (from chloroform-methanol); [α]$_D$−14° (c 0.9); ν$_{max}$ 1689 cm$^{-1}$; δ$_H$ 1.11 (3H, s, 13β-Me), 1.20 (3H, t, J 7.6 Hz, 15-CH$_2$CH$_3$), 2.40 (2H, m, 15-CH$_2$CH$_3$), 3.78 (3H, s, 3-OMe), 5.79 br (1H, s, 16-H), 6.64 (1H, d, J 2.8 Hz, 4-H), 6.73 (1H, dd, J 8.3 and 2.8 Hz, 2-H), and 7.22 (1H, d, J 8.3 Hz, 1-H); δ$_c$ 11.6 (C-15$^2$), 21.5 (C-18), 25.6 (C-11), 27.3 (C-7), 28.0 (C-12), 29.2 (C-15$^1$), 29.4 (C-6), 37.0 (C-8), 45.3 (C-9), 52.6 (C-13), 55.2 (3-OMe), 57.0 (C-12), 111.6 (C-2), 113.6 (C-4), 125.7 (C-16), 126.2 (C-1), 132.1 (C-10), 137.3 (C-5), 157.5 (C-3), 181.1 (C-15), and 212.2 (C-17) (Found: C, 81.1; H, 8.5%; M$^+$, 310. C$_{21}$H$_{26}$O$_2$ requires C, 81.25; H, 8.4%; M, 310).

15α-Ethyl-3-methoxy-15β-methylestra-1,3,5 (10)-trien-17-one (8)

A solution of methylmagnesium iodide (2.5 mmol) in dry diethyl ether (2.5 ml) [prepared at 20° C. from magnesium (60 mg; 2.5 mmol) and methyl iodide (0.16 ml; 2.5 mmol)] was cooled to 0° C. Copper(I) iodide (46 mg; 0.24 mmol) was added. After 5 min. at 0° C., a solution of the 15-ethyl-Δ$^{15}$-17-ketone (7) (150 mg; 0.48 mmol) in dry tetrahydrofuran (3 ml) was added. The mixture was stirred at 20° C. for 15 min. Saturated aqueous ammonium chloride and aqueous ammonia were added and the residue upon work-up (ethyl acetate) (150 mg; 96%) was crystallized from chloroform to give the 15α-ethyl-3-methoxy-15β-methylestra-1,3,5 (10)-trien-17-one (8) (127 mg; 81%); m.p. 110°–113° C. (from chloroform-methanol); [α]$_D$+90° (c 1.0); ν$_{max}$ 1724 cm$^{-1}$ (CO); δ$_H$ 0.89 (3H, t, J 7.4 Hz, 15α-CH$_2$CH$_3$), 1.12 (3H, s, 13β-Me), 1.25 (3H, s, 15β-Me), 1.36 and 1.76 (each 2H, degen. dq, J 14.8 and 3×7.4 Hz, 15α-CH$_2$CH$_3$), 2.18 and 2.44 (each 1H, d, J 19.4 Hz, 16α- and 16β-H), 2.88 (2H, m, 6-H$_2$), 3.77 (3H, s, 3-OMe), 6.62 (1H, d, J 2.9 Hz, 4-H), 6.71 (1H, dd, J 8.6 and 2.9 Hz, 2-H), and 7.20 (1H, d, J 8.6 Hz, 1-H); δ$_c$ 9.4 (C-15$^2$), 18.2 (C-18), 21.8 (C-15$^1$), 26.1 (C-11), 28.3 (C-7), 29.9 (C-6), 34.2 (C-12), 37.5 (C-8), 38.1 (15β-Me), 38.9 (C-15), 44.9 (C-9), 49.8 (C-16), 50.0 (C-13), 55.2 (3-OMe), 56.6 (C-14), 111.6 (C-2), 113.6 (C-4), 126.5 (C-1), 132.2 (C-10), 137.4 (C-5), 157.6 (C-3), and 220.4 (C-17) (Found: C, 81.2; H, 9.5%; M$^+$, 326. C$_{22}$H$_{30}$O$_2$ requires C, 80.9; H, 9.3%; M, 326).

15β-Isopropyl-3-methoxyestra-1,3,5 (10)-trien-17-one (9)

Copper(I) iodide-dimethyl sulfide (107 mg; 0.42 mmol) and hexamethylphosphoric triamide (1.1 ml; 6.3 mmol) were added to a solution of isopropylmagnesium bromide (4.25 mmol) [prepared at 0° C. from magnesium (102 mg; 4.25 mmol) and isopropyl bromide (0.4 ml; 4.26 mmol)] in dry diethyl ether (5 ml) at 0° C. After 5 min. at this temperature, a solution of the enone (1) (200 mg; 0.71 mmol) and chlorotrimethylsilane (0.8 ml; 6.30 mmol) in dry tetrahydrofuran was slowly added. The mixture was stirred at 0° C. for 20 min. Saturated aqueous ammonium chloride and aqueous ammonia were added. The residue upon work-up (ethyl acetate) (205 mg) was chromatographed on silica gel (20 g), and eluting in ethyl acetate-toluene (1:49) gives 15β-isopropyl-3-methoxyestra-1,3,5 (10)-trien-17-one (9) (201 mg; 87%), m.p. 104°–108° C. (from diisopropyl ether); $[\alpha]_D+106°$ (c 1.0); $v_{max}$ 1724 cm$^{-1}$ (CO); $\delta_H$ 0.96 and 1.10 (each 3H, d, J 6.4 Hz, 15β-CHMe$_2$), 1.08 (3H, s, 13β-Me), 1.92 (1H, dd, J 9.6 and 3.0 Hz, 14α-H), 2.41 (2H, m, 16-H2), 2.89 (2H, m, 6-H$_2$), 3.79 (3H, s, 3-OMe), 6.66 (1H, d, J 2.8-Hz, 4-H), 6.73 (1H, dd, J 8.4 and 2.8 Hz, 2-H), and 7.20 (1H, d, J 8.4 Hz, 1-H); $\delta_c$ 17.4 (C-18), 21.8 and 24.3 (15β-CHMe$_2$), 25.4 (C-11), 28.2 (C-7), 29.5 (C-6), 32.3 (C-8), 34.8 (C-12), 38.0 (C-15), 42.4 (C-9), 45.0 (C-16), 45.5 (C-14), 46.5 (C-13), 55.2 (3-OMe), 55.4 (15β-CHMe$_2$), 111.4 (C-2), 113.9 (C-4), 126.6 (C-1), 132.4 (C-10), 137.9 (C-5), 157.7 (C-3), and 222.8 (C-17) (Found: C, 80.5; H, 9.3%; M$^+$, 326. CH$_{22}$H$_{30}$O$_2$ requires C, 80.9; H, 9.3%; M, 326).

15-Isopropyl-3-methoxyestra-1,3,5(10),15-tetraen-17-one (10)

A solution of the 15β-isopropyl ketone (9) (210 mg; 0.64 mmol) in dry tetrahydrofuran (10 ml) was added to a solution of lithium diisopropylamide (3.2 mmol) [prepared at 0° C. from diisopropylamine (0.9 ml; 6.35 mmol) in tetrahydrofuran (2 ml) and butyl lithium (1.9 ml; 3.04 mmol)] at −78° C. After 30 min. at this temperature, chlorotrimethylsilane (1 ml; 7.88 mmol) was added. The mixture was allowed to warm to 0° C. over 20 min. Saturated aqueous ammonium chloride was added and the residue upon work-up (ethyl acetate) (242 mg) was dissolved in dry acetonitrile (20 ml). Palladium(II) acetate (140 mg; 0.62 mmol) was added and the mixture was heated to refluxing temperature for 20 min. The solution was cooled to 20° C., filtered and evaporated. The residue (230 mg) was chromatographed on silica gel (23 g), and eluting with ethyl acetate-toluene (1:19) gives 15isopropyl-3-methoxyestra-1, 3,5 (10), 15-tetraen-17 one (10) (170 mg; 81% from 9), m.p. 113°–116° C. (from chloroform-methanol); $[\alpha]_D-18°$ (C 1.0); $v_{max}$ 1690 Cm$^{-1}$ (CO); $\delta_H$ 1.10 (3H, s, 13β-Me), 1.16 and 1.22 (each 3H, d, J 6.6 Hz, 15-CHMe$_2$), 2.57 (1H, dd, J 11.2 and 2.7 Hz, 14α-H), 2.92 (2H, m, 6-H$_2$), 3.79 (3H, s, 3-OMe), 5.80 (1H, dd, J 2.7 and 1.2 Hz, 16-H), 6.65 (1H, d, J 2.7 Hz, 4-H), 6.74 (1H, dd, J 8.6 and 2.7 Hz, 2-H), and 7.24 (1H, d, J 8.6 Hz, 1-H); $\delta_c$21.1 (C-18), 21.6 and 21.7 (15-CHMe$_2$), 25.6 (C-11), 28.1 (C-7), 29.1 (C-6), 29.7 (C-8), 30.8 (15-CHMe$_2$), 37.4 (C-12), 45.4 (C-9), 52.6 (C-13), 55.2 (3-OMe), 56.3 (C-14), 111.6 (C-2), 113.6 (C-3), 123.9 (C-16), 126.3 (C-1), 132.2 (C-10), 137.2 (C-5), 157.7 (C-3), 185.7 (C-15), and 212.4 (C-17) (Found: C, 81.6; H, 8.9%; M$^+$, 324. C$_{22}$H$_{28}$O$_2$ requires C, 81.4; H, 8.7%; M, 324).

15α-Isopropyl-3-methoxy-15β-methylestra-1,3,5(10)-trien-17-one (11)

A solution of lithium dimethyl cuprate (0.61 mmol) in dry diethyl ether (1.5 ml) [prepared at 0° C. from copper(I) iodide (118 mg; 0.61 mmol) and methyl lithium (0.8 ml; 1.6 M; 1.28 mmol)] was cooled to −78° C. Triethylamine (0.1 ml; 0.72 mmol) and chlorotrimethylsilane (0.1 ml; 0.79 mmol) were sequentially added. Stirring at −78° C. was maintained for 5 min., before a solution of the isopropyl eneone (10) (100 mg; 0.31 mmol) in dry tetrahydrofuran (3 ml) was added dropwise. The reaction was stirred for a further 30 min. at 0° C. Saturated aqueous ammonium chloride and dilute HCl were added. To allow complete hydrolysis of the enol silyl ether, the mixture was stirred at 20° C. for 15 min. The residue upon work-up (ethyl acetate) (97 mg) was chromatographed on silica gel (10 g), and eluting with ethyl acetate-toluene (1:49) gives 15β-isopropyl-3-methoxy-15β-methylestra-1,3,5(10)-trien-17-one (11) (92 mg; 86%), m.p. 113°–115° C. (from diisopropyl ether); $[\alpha]_D+87°$ (C 0.9); $v_{max}$ 1724 Cm$^{-1}$ (CO); 6H (C$_6$D$_6$), 0.68 (6H, d, J 6.0 Hz, 15α-CHMe$_2$), 0.87 (3H, s, 15β-Me), 0.98 (3H, s, 13β-Me), 1.62 obsc (1H, q, J 6.0 Hz, 15β-CHMe$_2$), 1.95 and 2.15 (each 1H, d, J 19.1 Hz, 16α- and 16β-H), 2.68 (2H, m, 6-H$_2$), 3.44 (3H, s, 3-OMe), 6.70 (1H, d, J 2.6 Hz, 4-H), 6.79 (1H, dd, J 8.8 and 2.6 Hz, 2-H), and 7.09 (1H, d, J 8.8 Hz, 1-H); $\delta_H$ (CDCl$_3$) 0.87 and 0.89 (each 3H, d, J 6.7 Hz, 15α-CHMe$_2$), 1.13 (3H, s, 13β-Me), 1.32 (3H, s, 15β-Me), 2.23 obsc. (2H, d, J 18.7 Hz, 16α- and 16β-H), 2.87 (3H, m, 6-H$_2$), 3.77 (3H, s, 3-OMe), 6.68 (1H, d, J 2.8 Hz, 4-H), 6.75 (1H, dd, J 8.8 and 2.8 Hz, 2-H) and 7.20 (1H, d, J 8.8 Hz, 1-H); $\delta_c$ 17.8 (C-18), 18.4 and 18.8 (15α-CHMe$_2$), 23.0 (C-11), 26.1 (C-7), 27.8 (15β-Me), 30.0 (C-8), 34.5 (C-12), 36.9 (15α-CHMe$_2$), 37.7 (C-6), 41.5 (C-15), 44.6 (C-9), 45.0 (C-16), 49.9 (C-13), 51.6 (C-14), 55.2 (3-OMe), 111.6 (C-2), 113.6 (C-4), 126.5 (C-1), 132.2 (C-10), 137.4 (C-5), 157.6 (C-3), and 220.3 (C-17) (Found: C, 81.2; H, 9.6%; M$^+$, 340. C$_{23}$H$_{32}$O$_2$ requires C, 81.1; H, 9.5%; M, 340).

3-Methoxy-15,15-dimethylestra-1,3,5(10)-trien-17β-ol (12)

Lithium aluminum hydride (30 mg; 0.79 mmol) was added to a solution of the dimethyl ketone (4) (50 mg; 0.16 mmol) in dry tetrahydrofuran (2 ml) at 0° C. The mixture was stirred at 0° C. for 5 min. Saturated aqueous sodium hydrogen carbonate was added and the mixture was filtered. Work-up of the filtrate (ethyl acetate) gave 3-methoxy-15, 15-dimethylestra-1,3,5(10)-trien-17β-ol (12) (43 mg; 85%), m.p. 87°–91° C. (from chloroform-hexane), $[\alpha]_D+75°$ (c 1.1); $v_{max}$ 3606 cm$^{-1}$ (OH); δ0.92 (3H, s, 13β-Me), 1.06 (1H, d, J 11.2 Hz, 14α-H), 1.11 and 1.14 (each 3H, s, 15α- and 15β-Me), 1.61 and 1.90 (each 1H, dd, J 13.0 and 10.2, and 13.0 and 7.9 Hz, 16α- and 16β-H), 2.86 (2H, m, 6-H$_2$), 3.71 (1H, dd, J 10.2 and 7.9 Hz, 17α-H), 3.77 (3H, s, 3-OMe), 6.62 (1H, d, J 2.7 Hz, 4-H), 6.71 (1H, dd, J 8.6 and 2.7 Hz, 2-H), and 7.21 (1H, d, J 8.6 Hz, 1-H); $\delta_c$ 13.5 (C-18), 25.6 (15-Me), 26.1 (C-11), 28.5 (C-7), 29.9 (C-6), 35.0 (C-12), 36.2 (C-15), 37.1 (C-8), 38.8 (15-Me), 44.9 (C-9), 45.6 (C-13), 50.1 (C-16), 55.2 (3-OMe), 58.1 (C-14), 79.8 (C-17), 111.4 (C-2), 113.6 (C-4), 126.3 (C-1), 132.9 (C-10), 137.7 (C-5), and 157.5 (C-3) (Found: C, 80.0; H, 9.5%; M$^+$, 314. C$_{21}$H$_{30}$O$_2$ requires C, 80.2; H, 9.6%; M, 314).

15β-Ethyl-3-methoxy-15β-methylestra-1,3,5 (10)-trien-17α-ol (13)

Lithium aluminum hydride (58 mg; 0.31 mmol) was added to a solution of the 15β-ethyl-15β-methyl ketone (5) (100 mg; 0.31 mmol) in dry tetrahydrofuran (2 ml) at 0°C. The solution was stirred at 0° C. for 5 min. Saturated aqueous ammonium chloride was added and the mixture was filtered. Standard work-up of the filtrate gave 15β-ethyl-3-methoxy-15α-methylestra-1,3,5(10)-trien-17β-ol (13) (92 mg; 90%), as an oil, $[\alpha]_D+70°$ (c 1.0); $v_{max}$ 3604 cm$^{-1}$ (OH); $\delta_H$ 0.88 (3H, t, J 7.2 Hz, 15β-CH$_2$CH$_3$), 0.90 (3H, s, 15α-Me), 1.10 (3H, s, 13β-Me), 1.51 obsc (2H, m, 15α-CH$_2$CH$_3$), 1.73 obsc (2H, m, 16α- and 16β-H), 2.84 (2H, m, 6-H$_2$), 3.74 (1H, dd, J 9.9 and 8.2 Hz, 17α-H), 3.78 (3H, s, 3-OMe), 6.63 (1H, d, J 2.8 Hz, 4-H), 6.71 (1H, dd, J 8.4 and 2.8 Hz, 2-H), and 7.21 (1H, d, J 8.4 Hz, 1-H); δ$_c$ 8.6 (C-15$^2$), 13.9 (C-18), 25.9 (C-15$^1$), 28.6 (C-11), 29.0 (C-7), 29.9 (C-6), 30.3 (C-12), 36.8 (C-8), 39.0 (15α-Me), 40.0 (C-15), 45.2 (C-9), 45.5 (C-4), 55.2 (3-OMe), 59.6 (C-13), 79.5 (C-16), 80.0 (C-17), 111.4 (C-2), 113.6 (C-4), 126.2 (C-1), 133.0 (C-10), 137.7 (C-5), and 157.5 (C-3).

15α-Ethyl-3-methoxy-15β-methylestra-1,3,5 (10)-trien-17β-ol (14)

Lithium aluminum hydride (48 mg; 1.26 mmol) was added to a solution of the 15α-ethyl-15β-methyl ketone (8) (80 mg; 0.25 mmol) in dry tetrahydrofuran at 0° C. Low temperature stirring was maintained for 5 min. Saturated aqueous sodium hydrogen carbonate was added and the mixture was filtered. Standard work-up of the filtrate (ethyl acetate) gave 15α-ethyl-3-methoxy-15β-methylestra-1,3,5 (10)-trien-17β-ol (14) (75 mg; 89%), m.p. 133°–136° C. (from chloroform-methanol); [α]$_D$+67° (c 0.9); ν$_{max}$ 3604 cm$^{-1}$ (OH); δ$_H$ 0.88 (3H, t, J 7.2 Hz, 15β-CH$_2$CH$_3$), 0.93 (3H, s, 15β-Me), 1.06 (3H, s, 13β-Me), 1.10 (1H, d, J 11.1 Hz, 14α-H), 1.32 obsc (2H, m, 15β-CH$_2$CH$_3$), 1.39 and 2.04 (each 1H, dd, J 13.2 and 10.0, and 13.2 and 7.9 Hz, 16α- and 16β-H), 2.84 (2H, m, 6-H$_2$), 3.60 (1H, dd, J 10.0 and 7.9 Hz, 17α-H), 3.77 (3H, s, 3-OMe), 6.61 (1H, d, J 2.9 Hz, 4-H), 6.70 (1H, dd, J 8.6 and 2.9 Hz, 2-H), and 7.20 (1H, d, J 8.6 Hz, 1-H); δ$_c$ 9.4 (C-15$^2$), 13.9 (C-18), 23.7 (C-15$^1$), 26.1 (C-11), 28.6 (C-7), 29.9 (C-6), 37.1 (C-12), 37.7 (C-8), 38.9 (15β-Me), 39.7 (C-15), 45.0 (C-9), 45.6 (C-14), 55.2 (3-OMe), 55.6 (C-13), 79.3 (C-16), 80.2 (C-17), 111.4 (C-2), 113.6 (C-4), 126.3 (C-1), 133.0 (C-10), 137.7 (C-5), and 157.5 (C-3) (Found: C, 80.0; H, 9.7%; M$^+$, 328. C$_{22}$H$_{32}$O$_2$ requires C, 80.4; H, 9.8%; M, 328).

15α-Isopropyl-3-methoxy15β-methylestra-1,3,5(10)-trien-17β-ol (15)

Lithium aluminum hydride (35 mg; 0.92 mmol) was added to a solution of the 15α-isopropyl-15β-methyl ketone (11) (63 mg; 0.19 mmol) in dry tetrahydrofuran (4 ml) at 0° C. After 10 min. at this temperature, saturated aqueous sodium hydrogen carbonate was added. The mixture was filtered, and the clear solution was given the standard work-up (ethyl acetate) to give 15α-isopropyl-3-methoxy-15β-methylestra-1,3,5(10)-trien-17β-ol (15) (60 mg; 95%), [α]$_D$+54° (c 1.3); ν$_{max}$ 3604 cm$^{-1}$ (OH); ν$_H$ (200MHz), 0.88 and 0.92 (each 3H, d, J 6.8 Hz, 15α-CHMe$_2$), 0.96 (3H, s, 13β-Me), 1.13 (3H, s, 15β-Me), 1.73 (1H, dd, J 13.4 and 10.2 Hz, 16-H), 2.13 (1H, dd, J 13.4 and 7.9 Hz, 16-H), 3.54 (1H, dd, J 10.2 and 7.9 Hz, 17α-H), 3.78 (3H, s, 3-OMe), 6.64 (1H, dd, J 2.7 Hz, 4-H), 6.71 (1H, dd, J 8.5 and 2.7 Hz, 2-H), and 7.22 (1H, d, J 8.5 Hz, 1-H); δ$_c$ 14.1 (C-18), 18.2 and 18.6 (15α-CHMe$_2$), 23.6 (C-11), 26.2 (C-7), 28.5 (15β-Me), 29.9 (C-8), 36.6 (C-12), 37.3 (15α-CHMe$_2$), 39.3 (C-6), 40.7 (C-15), 42.7 (C-13), 44.7 (C-9), 45.0 (C-16), 51.8 (C-14), 55.2 (3-OMe), 80.8 (C-17), 111.4 (C-2), 113.6 (C-4), 126.3 (C-1), 133.0 (C-10), 137.6 (C-5), and 157.7 (C-3) (Found: C, 80.4; H, 9.9%; M$^+$, 342. C$_{23}$H$_{34}$O$_2$ requires C, 80.65; H, 10.0%; M, 342).

Examples 2–5

3-Demethylation of 15,15-dialkyl-17β-alcohols (12–15)

Example 2

Representative Procedure: Diisobutylaluminum hydride (0.5 ml; 1.5M; 0.75 mmol) was added to a solution of the 15,15-dimethyl-17β-alcohol (12) in dry toluene (5 ml). The solution was heated to refluxing temperature for 24 h. The mixture was cooled to 0° C., saturated aqueous ammonium chloride was added, and the aqueous phase was further acidified with dilute HCl. The standard work-up (ethyl acetate) gave 15,15-dimethylestra-1,3,5 (10)-triene-3,17β-diol (16) (43 mg; 90%), m.p. 167–170 (from ethyl acetate); [α]$_D$+49° (C 1.1 ethanol) (Found; C, 79.6; H, 9.3%; M$^+$, 300. C$_{20}$H$_{28}$O$_2$ requires C, 80.0; H, 9.4%; M, 300).

Example 3

15β-Ethyl-15α-methylestra-1,3,5 (10)—triene-3,17β-diol (17)

m.p. 132°–136° C. (from ethyl acetate); [α]$_D$+54° (c 1.0 in ethanol (Found: C, 80.4; H, 9.5%; M$^+$, 314. C$_{21}$H$_{32}$O$_2$ requires C, 80.2; H, 9.6%; M, 314).

Example 4

15α-Ethy15β-methylestra-1,3,5 (10)-triene-3,17β-diol (18)

obtained as a foam; [α]$_D$+59° (c 1.0 in ethanol) (Found: C, 79.8; H, 9.5%; M$^+$, 314. C$_{21}$H$_{30}$O$_2$ requires C, 80.2, H, 9.6%; M, 314).

Example 5

15α-iso-Propyl-15β-methylestra-1,3,5 (10)-triene-3,17β-diol (19)

m.p. 201°–205° C. (from ethyl acetate); [α]$_D$+71° (c 1.0 in tetrahydrofuran) (Found: C, 80.7; H, 9.8%; M$^+$, 328. C$_{22}$H$_{32}$O$_2$ requires C, 80.4; H, 9.8%; M, 328).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula IIa

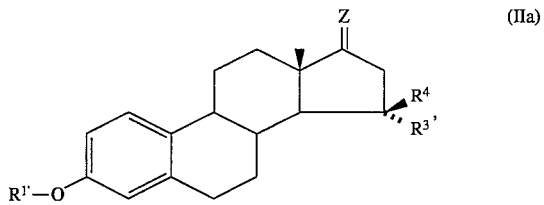

wherein

R$^1$ is a straight-chain alkyl having 1–10 carbon atoms or a branched-chain alkyl group having 3–10 carbon atoms;

R$^3$ and R$^4$, independently of one another, are each a straight-chain alkyl having 1–10 carbon atoms or a branched-chain alkyl having 3–10 carbon atoms; and Z is an α-hydrogen atom and a β-hydroxy group or a keto-oxygen atom.

2. A compound according to claim 1, wherein R$^3$ and R$^4$, independently of one another, are each methyl, ethyl, propyl, isopropyl, butyl, isobutyl or tert-butyl.

3. A compound according to claim 2, wherein R$^3$ and R$^4$ are each methyl.

4. A compound according to claim 1, wherein said compound is 3-methoxy-15,15-dimethylestra-1,3,5(10)-triene-17-one, 15β-ethyl-3-methoxy-15α-methylestra-1,3,5(10)-triene-17-one, 15α-ethyl-3-methoxy- 15βmethylestra-1,3, 5(10)-triene-17-one, or 15α-isopropyl-3-methoxy-15β-methylestra-1,3,5(10)-triene-17-one.

5. A compound according to claim 1, wherein Z is an α-hydrogen atom and a β-hydroxy group.

6. A compound according to claim 1, wherein Z is a keto oxygen atom.

7. A compound according to claim 1, wherein $R^1$ is methyl.

8. A compound according to claim 3, wherein Z is an α-hydrogen atom and a β-hydroxy group.

9. A compound according to claim 3, wherein Z is a keto oxygen atom.

10. A compound according to claim 1, wherein $R^3$ and $R^4$, independently of one another, are each ethyl, propyl, isopropyl, butyl, isobutyl or tert-butyl.

11. A compound according to claim 2, wherein $R^3$ is ethyl, propyl, isopropyl, butyl, isobutyl or tert-butyl.

12. A compound according to claim 2, wherein $R^4$ is ethyl, propyl, isopropyl, butyl, isobutyl or tert-butyl.

13. A compound according to claim 1, wherein said compound is 3-methoxy- 15,15-dimethylestra-1,3,5(10)-triene-17ol, 15β-ethyl-3-methoxy-15α-methylestra- 1,3,5(10)-triene-17β-ol, 15α-methoxy-15β-methylestra-1,3,5(10)-triene-17β-ol, or 15α-isopropyl-3-methoxy-15β-methylestra-1,3,5(10)-triene-17β-ol.

* * * * *